(12) United States Patent
Hu et al.

(10) Patent No.: US 10,985,003 B2
(45) Date of Patent: Apr. 20, 2021

(54) ANALYSIS METHOD FOR DETERMINING HALOGENS IN GEOLOGICAL SAMPLES BY ICP-MS

(71) Applicant: China University of Geosciences, Wuhan, Hubei (CN)

(72) Inventors: Zhaochu Hu, Hubei (CN); Tao He, Hubei (CN); Wen Zhang, Hubei (CN); Haihong Chen, Hubei (CN); Ming Li, Hubei (CN); Yongsheng Liu, Hubei (CN)

(73) Assignee: China University of Geosciences, Wuhan, Wuhan (CN)

( * ) Notice: Subject to any disclaimer, the term of this patent is extended or adjusted under 35 U.S.C. 154(b) by 0 days.

(21) Appl. No.: 16/830,487

(22) Filed: Mar. 26, 2020

(65) Prior Publication Data
US 2020/0312648 A1 Oct. 1, 2020

(30) Foreign Application Priority Data
Mar. 28, 2019 (CN) .......................... 201910244943.1

(51) Int. Cl.
*H01J 49/00* (2006.01)
*H01J 49/10* (2006.01)
*G01N 33/24* (2006.01)
*H01J 49/04* (2006.01)
*H01J 49/26* (2006.01)

(52) U.S. Cl.
CPC ............ *H01J 49/105* (2013.01); *G01N 33/24* (2013.01); *H01J 49/0459* (2013.01); *H01J 49/0468* (2013.01); *H01J 49/26* (2013.01)

(58) Field of Classification Search
CPC .. H01J 49/105; H01J 49/0459; H01J 49/0468; H01J 49/26; G01N 33/24; G01N 1/44; G01N 27/62
USPC ........................................ 250/281, 282, 288
See application file for complete search history.

(56) References Cited

FOREIGN PATENT DOCUMENTS

| CN | 102854053 A | * | 1/2013 |
| CN | 102854053 A | | 1/2013 |
| TW | 201333458 A | | 8/2013 |

* cited by examiner

*Primary Examiner* — Michael Maskell

(57) ABSTRACT

The present invention provides an analysis method for determining halogens in geological samples by ICP-MS. The method includes following steps: weighing a geological sample and ammonium bifluoride in a sample dissolving tank, tightening the sample dissolving tank, and shaking; then heating the sample dissolving tank in a drying oven, and setting a temperature of the drying oven as 200-220° C. and heating time as 1-2 hours; cooling the sample dissolving tank to room temperature so as to obtain a solid mixture after heating is ended, adding ammonium hydroxide into the solid mixture, centrifuging, removing a precipitate, and collecting the supernatant; adding an internal standard solution into the supernatant, and uniformly mixing; and optimizing the ICP-MS to an optimal state, testing content of chlorine in the supernatant under a condition of medium resolution m/Δm=4000, and testing content of bromine and iodine in the supernatant under a condition of low resolution m/Δm=300.

8 Claims, 1 Drawing Sheet

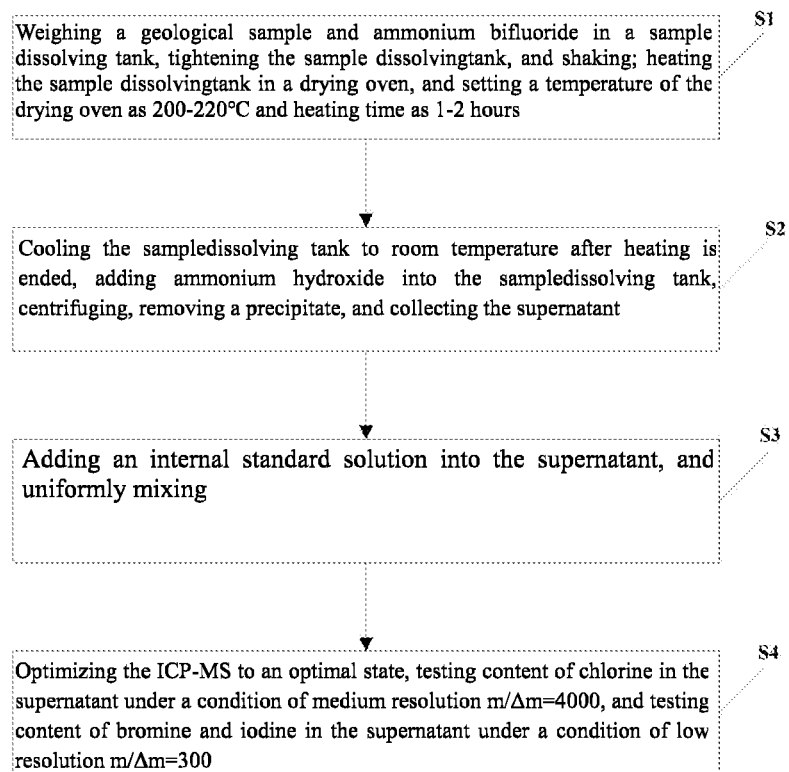

ANALYSIS METHOD FOR DETERMINING HALOGENS IN GEOLOGICAL SAMPLES BY ICP-MS

CROSS-REFERENCE TO RELATED APPLICATIONS

This application claims the benefit of priority from Chinese Patent Application No. 201910244943.1, filed on Mar. 28, 2019. The content of the aforementioned application, including any intervening amendments thereto, is incorporated herein by reference in its entirety.

TECHNICAL FIELD

The present invention relates to the technical field of chemical analysis, and particularly relates to an analysis method for determining halogens in geological samples by ICP-MS (Inductively Coupled Plasma Mass Spectrometry).

BACKGROUND OF THE PRESENT INVENTION

Halogen content and isotope ratios of halogens in geological samples such as rock, soil and sediments may provide key information for researches on evolutionary history of the earth, palaeoenvironment and paleoclimate reconstruction, formation mechanisms of ore deposits, and the like. For example, chlorine may control composition of rock magma and hydrothermal fluid, thereby influencing migration of ore-forming metals and formation of ore deposits in earth crust. Accurate determination of the halogens in the geological samples is of great importance for promoting the development of geochemistry. However, with respect to low-content halogens in the geological samples, effective analysis means still lacks. Developing an efficient analytical testing method for low-content halogens in the geological samples is in an urgent need of analyzing geochemical development at present.

Sample pretreatment is the key for analysis of the geological samples, and this process is particularly important to halogen analysis in the geological samples. Since the halogens have high volatility under acidic conditions, and a conventional geological sample pretreatment method (such as inorganic acid digestion) may cause serious losses of the halogens, the conventional inorganic acid digestion cannot be applied to analytical determination of the halogens. At present, sample pretreatment technologies for halogens mainly include pyrolysis and alkali fusion. The pyrolysis is one of the extraction methods used most widely currently. A sample is pyrolyzed to release halogens at high temperature (1000-1200° C.), the released halogen is introduced into alkaline capture liquor (sodium hydroxide, sodium sulfite, etc.) by carrier gases (such as oxygen), and then halogens in the capture liquor are analyzed by IC (Ion Chromatography) or ICP-MS (Inductively Coupled Plasma Mass Spectrometry). According to the method, the halogens are separated from the matrix; a matrix effect is small, but pyrolysis temperature, types of fluxing agents and the type of the capture liquor have great influences on recovery (82-100%) of the halogens. In addition, the pyrolysis method is high in time consumption; and apparatuses need to be cleaned by plenty of time between every two samples, which is not beneficial for the analytical test of large-scale samples. The alkali fusion is performed as follows: fluxing agents ($ZnO + Na_2CO_3$) and samples are fused at high temperature (600-900° C.), a fused cake is dissolved with deionized water, and then halogens in the supernatant are tested by the IC or ICP-MS. However, due to use of the fluxing agents, many positive ions are introduced and need to be treated with cation exchange resins, and the process is complicated. In addition, a dilute ammonia water closed sample dissolving method is performed as follows: bromine and iodine in the samples are directly extracted in a closed environment by adopting dilute ammonia water. The method is simple in operation and low in blank value, but only applicable to bromine and iodine bonded to organic matters in the soil and sediments. For rock enriched in silicate minerals, the dilute ammonia water cannot effectively damage crystal lattices of the minerals, and thus cannot extract the halogens in the minerals. The procedure of the method generally takes lot of time up to over ten hours. In addition to the above methods, neutron activation, radiochemical neutron activation and combination of neutron activation and rare-gas mass spectrometry are also methods for analyzing the low-content halogens in the geological samples at present. However, since neutron activation reactors need to be used, the use of the methods is limited.

The ICP-MS has analytical characteristics of high sensitivity, good precision, low detection limit and capacity of providing isotopic information by virtue of multi-element simultaneous detection, and has been widely applied to analysis of trace elements in the geological samples. However, since ionization energy of halogens is relatively high, in the traditional quadrupole ICP-MS, sensitivity of the halogens is low, and determination of the low-content halogens cannot be well performed. Further, low resolution ($m/\Delta m=300$) of the quadrupole ICP-MS cannot eliminate interference of multi-atomic ions to the halogens, such as interference of $^{18}O^{16}O^{1}H$ to $^{35}Cl$.

Therefore, developing a rapid analysis method for determining the halogens in the geological samples by ICP-MS is a problem that urgently needs to be solved in current geochemical analysis.

SUMMARY OF THE PRESENT INVENTION

In view of this, the present invention provides an analysis method for determining halogens in geological samples by ICP-MS. The method overcomes halogen loss in a pretreatment process of the geological samples, and can effectively increase digestion efficiency of the geological samples, decrease analysis time and achieve the aim of accurately determining low-content halogens in the geological sample by the ICP-MS.

The analysis method for determining halogens in geological samples by ICP-MS provided by the present invention includes the following steps:

step S1, weighing a geological sample and ammonium bifluoride in a sample dissolving tank, tightening the sample dissolving tank, and shaking; and heating the sample dissolving tank in a drying oven, and setting a temperature of the drying oven as 200-220° C. and heating time as 1-2 hours;

step S2, cooling the sample dissolving tank to room temperature so as to obtain a solid mixture after heating is ended, adding ammonium hydroxide into the solid mixture, centrifuging, removing a precipitate, and collecting the supernatant;

step S3, adding an internal standard solution into the supernatant, and uniformly mixing; and step S4, optimizing the ICP-MS to an optimal state, testing content of chlorine in the supernatant under a condition of medium resolution $m/\Delta m=4000$, and testing content of bromine and iodine in the supernatant under a condition of low resolution $m/\Delta m=300$.

Further, in the step S1, the geological sample is pretreated, and the pretreatment process is as follows: the geological sample is physically crushed into powder and then sieved by a 200-mesh sieve.

Further, in the step S1, a mass ratio of the geological sample to the ammonium bifluoride is 1:(3-8).

Further, in the step S1, the sample dissolving tank is a new sample dissolving tank made of Teflon. The sample dissolving tank needs to be soaked with high-purity nitric acid for 24 hours before use, and is cleaned with deionized water and then aired.

Further, in the step S1, the geological sample includes rock, soil or sediments; and the rock includes granite, shale, basalt or andesite.

Further, in the step S2, the ammonium hydroxide has a concentration of 5% v/v, and is prepared by diluting ammonium hydroxide of a chromatographically pure level or higher purity with deionized water.

Further, in the step S2, a centrifugal speed is 2500 r/min, and centrifugation time is 25 minutes.

Further, in the step S3, the internal standard solution is a 10 ng/g Te (tellurium) solution, and a medium of the 10 ng/g Te (tellurium) solution is the 5% v/v ammonium hydroxide.

Further, in the step S4, the optimal state of the optimized ICP-MS is that a signal of element. In having a concentration of 1 ng/g is up to $10^6$ cps, and oxide yield $CeO^+/Ce^+$ is less than 2%.

The principle of the analysis method provided by the present invention is as follows: the ammonium bifluoride may digest the silicate minerals; and when the temperature is increased to be higher than 200° C., the ammonium bifluoride is decomposed into HF and $NH_3$. The HF is used for digesting the geological sample, and the $NH_3$ may bond to halogens released in the digestion process. Under a condition of 200-220° C., the halogens are reserved in the sample dissolving tank in a form of ammonium salt. The whole process only needs 1-2 hours.

Compared with the prior art, the present invention achieves beneficial effects as follows:

(1) In the method provided by the present invention, the geological samples are completely digested and extraction of the halogens only needs 1-2 hours; the efficiency is increased by 10-20 times compared with that of the traditional sample dissolving method, and capacity of the method provided by the present invention for dissolving refractory silicate minerals is incomparable to other methods.

(2) The apparatuses used in the method provided by the present invention are extremely simple; experimental conditions are mild; no closed sample dissolving bomb is not needed; any complicated equipment (such as a miniature reactor) or harsh experimental condition (a temperature of 1200° C. needed by pyrolysis) is also not needed; and a general laboratory may meet the demand.

(3) Strong acid is not used in the method provided by the present invention; the solid reagent ammonium bifluoride and a small amount of ammonium hydroxide need to be used only; and the method has the advantages of simple procedure, safety, environmental protection, low blank and low cost.

(4) A high-resolution inductively coupled plasma mass spectrometer is adopted in the method provided by the present invention, and interference of multi-atomic ions to halogen analysis and determination can be effectively avoided, such as interference of $^{18}O^{16}O^1H$ to $^{35}Cl$; and high sensitivity ($10^6$ cps/ppb) of the high-resolution inductively coupled plasma mass spectrometer provides guarantee for analytical test of the low-content halogens.

(5) Measured values of the halogens in various geological samples analyzed by the method provided by the present invention well coincide with reference values, and the method has excellent application prospects in halogen analysis of the geological samples.

BRIEF DESCRIPTION OF THE DRAWINGS

FIG. 1 is a flow chart of an analysis method for determining halogens in geological samples by ICP-MS in the present invention.

DETAILED DESCRIPTION OF THE PRESENT INVENTION

To make purposes, technical solutions and advantages of the present invention more clear, embodiments of the present invention are further described below in combination with drawings.

Referring to FIG. 1, embodiments of the present invention provide an analysis method for determining halogens in geological samples by ICP-MS, and the method includes the following steps:

step S1, a geological sample was physically crushed into powder in advance; the powder was sieved by a 200-mesh sieve; then the geological sample and ammonium bifluoride were weighed in a sample dissolving tank according to a mass ratio of 1:(3-8); the sample dissolving tank was tightened, and shaking was performed; the sample dissolving tank was heated in a drying oven; and a temperature of the drying oven was set as 200-220° C. and heating time was set as 1-2 hours;

step S2, the sample dissolving tank was cooled to room temperature so as to obtain a solid mixture after heating was ended; ammonium hydroxide having a concentration of 5% v/v was added into the sample dissolving tank; centrifugation was performed at a rate of 2500 r/min for 25 minutes; a precipitate was removed; and the supernatant was collected;

step S3, a 10 ng/g Te solution was added into the supernatant, and uniform mixing was performed; and step S4, the ICP-MS was optimized until a signal of element. In having a concentration of 1 ng/g was up to $10^6$ cps and oxide yield $CeO^+/Ce^+$ was less than 2%; then content of chlorine in the supernatant was tested under a condition of medium resolution $m/\Delta m=4000$; and content of bromine and iodine in the supernatant was tested under a condition of low resolution $m/\Delta m=300$.

The analysis method for determining halogens in the geological samples by ICP-MS provided by the present invention is described in detail below in combination with embodiments.

In the embodiments below, the source of used raw materials is as follows:

top-grade pure ammonium bifluoride (purified by secondary sub-boiling distillation, analytically pure, Chemical Reagent Co., Ltd., China National Pharmaceutical Group);

chromatographically pure ammonium hydroxide (Aladdin's Reagent (Shanghai) Co., Ltd.);

ultrapure water (U.S Millipore Corporation, Millipore-Simplicity personal ultrapure water system, effluent resistivity of 18.2 MΩ/cm);

tellurium elemental standard solution (National Steel Material Testing Center, 1000 μg/ml);

PFA sample dissolving tank (Savillex Company);

high-resolution inductively coupled plasma mass spectrometer ELEMENT XR (Thermo Fisher Scientific Company, Germany).

Embodiment 1

1) a basalt (BHVO-2) sample was physically crushed to 200 meshes (sieved: 0.074 mm) so as to obtain test sample powder;

2) 300 mg of ammonium bifluoride and 100±1 mg of the basalt (BHVO-2) sample powder were weighed; the materials were added into a clean PFA sample dissolving tank; the PFA sample dissolving tank was tightened, manually shaken for half a minute and then put in an electronic drying oven; and the temperature was set as 220° C. and time was set as 2 hours;

3) the PFA sample dissolving tank was cooled to room temperature after heating was ended; then the geological sample and ammonium bifluoride in the PFA sample dissolving tank were mixed together; a white solid cake mixture was obtained; the PFA sample dissolving tank was taken out; 25 mL of ammonium hydroxide having a concentration of 5% v/v was added; and the mixture was transferred into a 50 mL centrifuge tube; and 4) the centrifuge tube was placed in a centrifugal machine; centrifugation was performed at a speed of 2500 r/min for 25 minutes; 2 mL of supernatant was collected into a 4 mL PET (polyethylene terephthalate) injector tube after centrifugation; 20 µL of tellurium (Te) elemental standard solution (1000 µg/mL) was added so as to obtain a to-be-tested analytical solution; and the solution was detected by utilizing the inductively coupled plasma mass spectrometer, wherein detection results were shown in Table 1.

Embodiment 2

The difference of Embodiment 2 and Embodiment 1 is only as follows: the geological sample selected in Embodiment 2 is basalt (BCR-2); and the rest is basically the same as Embodiment 1.

Detection results of Embodiment 2 are shown in Table 1.

Embodiment 3

The difference of Embodiment 3 and Embodiment 1 is only as follows: the geological sample selected in Embodiment 3 is granite (GSP-2); and the rest is basically the same as Embodiment 1.

Detection results of Embodiment 3 are shown in Table 1.

Embodiment 4

The difference of Embodiment 4 and Embodiment 1 is only as follows: the geological sample selected in Embodiment 4 is andesite (AGV-2); and the rest is basically the same as Embodiment 1.

Detection results of Embodiment 4 are shown in Table 1.

Embodiment 5

1) a shale (GSR-5) sample was physically crushed to 200 meshes (sieved: 0.074 mm) so as to obtain test sample powder;

2) 300 mg of ammonium bifluoride and 100±1 mg of the shale (GSR-5) sample powder were weighed; the materials were added into a clean PFA sample dissolving tank; the PFA sample dissolving tank was tightened, manually shaken for half a minute and then put in an electronic drying oven; and the temperature was set as 220° C. and time was set as 1 hour;

3) the PFA sample dissolving tank was cooled to room temperature after heating was ended; then the geological sample and ammonium bifluoride in the PFA sample dissolving tank were mixed together; a black solid cake mixture was obtained; the PFA sample dissolving tank was taken out; 25 mL of ammonium hydroxide having a concentration of 5% v/v was added; and the mixture was transferred into a 50 mL centrifuge tube; and 4) the centrifuge tube was placed in a centrifugal machine; centrifugation was performed at a speed of 2500 r/min for 25 minutes; 2 mL of supernatant was collected into a 4 mL PET injector tube after centrifugation; 20 µL of a tellurium (Te) elemental standard solution (1000 µg/mL) was added so as to obtain a to-be-tested analytical solution; and the solution was detected by utilizing the inductively coupled plasma mass spectrometer, wherein detection results were shown in Table 1.

Embodiment 6

1) a loess (GSS-8) sample was physically crushed to 200 meshes (sieved: 0.074 mm) so as to obtain test sample powder;

2) 300 mg of ammonium bifluoride and 50±1 mg of the loess (GSS-8) sample powder were weighed; the materials were added into a clean PFA sample dissolving tank; the PFA sample dissolving tank was tightened, manually shaken for half a minute and then put in an electronic drying oven; and the temperature was set as 220° C. and time was set as 2 hours;

3) the PFA sample dissolving tank was cooled to room temperature after heating was ended; then the geological sample and ammonium bifluoride in the PFA sample dissolving tank were mixed together; a black solid cake mixture was obtained; the PFA sample dissolving tank was taken out; 25 mL of ammonium hydroxide having a concentration of 5% v/v was added; and the mixture was transferred into a 50 mL centrifuge tube; and 4) the centrifuge tube was placed in a centrifugal machine; centrifugation was performed at a speed of 2500 r/min for 25 minutes; 2 mL of supernatant was collected into a 4 mL PET injector tube after centrifugation; 20 µL of a tellurium (Te) elemental standard solution (1000 µg/mL) was added so as to obtain a to-be-tested analytical solution; and the solution was detected by utilizing the inductively coupled plasma mass spectrometer, wherein detection results were shown in Table 1.

Embodiment 7

The difference of Embodiment 7 and Embodiment 6 is only as follows: the geological sample selected in Embodiment 7 is loess (GSS-25); and the rest is basically the same as Embodiment 6.

Detection results of Embodiment 7 are shown in Table 1.

Embodiment 8

The difference of Embodiment 8 and Embodiment 6 is only as follows: the geological sample selected in Embodiment 8 is sediment (GSD-7a); and the rest is basically the same as Embodiment 6.

Detection results of Embodiment 8 are shown in Table 1.

Embodiment 9

The difference of Embodiment 9 and Embodiment 6 is only as follows: the geological sample selected in Embodiment 9 is sediment (GSD-11); and the rest is basically the same as Embodiment 6.

Detection results of Embodiment 9 are shown in Table 1.

Table 1 lists determination results and references values of chlorine, bromine and iodine in the various geological samples in Embodiments 1-9. It can be known from data in Table 1 that, for the analyzed geological samples of different types, the measured values of the chlorine, bromine and iodine well coincide with the reference values, which indicates that the ammonium bifluoride extraction method proposed by the present invention is high in reliability.

TABLE 1

Determination Results and References Values of Chlorine, Bromine and Iodine in Various Geological Samples in Embodiments 1-9

| Sample | Sample type | Cl recommended value (μg/g) | Cl measured value (μg/g) | Br recommended value (μg/g) | Br measured value (μg/g) | I recommended value (μg/g) | I measured value (μg/g) |
|---|---|---|---|---|---|---|---|
| BHVO-2 | basalt | 81-104 | 87 ± 3 | 0.24-0.295 | 0.28 ± 0.02 | 0.016-0.307 | 0.047 ± 0.005 |
| BCR-2 | basalt | 89-112 | 97 ± 4 | 0.144-0.192 | 0.16 ± 0.02 | 0.017-0.082 | 0.023 ± 0.009 |
| GSP-2 | granite | 363-400 | 389 ± 47 | 0.077-0.117 | 0.57 ± 0.06 | 0.020-0.075 | 0.013 ± 0.002 |
| AGV-2 | andesite | 61-83 | 84 ± 4 | 0.101-0.244 | 0.27 ± 0.03 | 0.007-0.197 | 0.013 ± 0.003 |
| GSR-5 | shale | 40-41 | 50 ± 5 | 0.4 | 0.51 ± 0.02 | 0.24 | 0.14 ± 0.01 |
| GSS-8 | loess | 68 ± 12 | 64 ± 3 | 2.00-2.5 | 2.19 ± 0.12 | 1.57-1.96 | 1.91 ± 0.05 |
| GSS-25 | loess | 61 ± 5 | 63 ± 5 | 2.6-2.69 | 2.52 ± 0.20 | 1.49-1.5 | 1.50 ± 0.10 |
| GSD-7a | sediment | 51 ± 10 | 39 ± 7 | 0.95-1.3 | 1.05 ± 0.11 | 0.35-0.54 | 0.38 ± 0.04 |
| GSD-11 | sediment | 290 ± 26 | 276 ± 13 | 1.76-2.53 | 1.88 ± 0.10 | 1.89-2.29 | 1.86 ± 0.10 |

Without conflict, the above embodiments and features in the embodiments herein may be combined with each another.

The above only describes preferred embodiments of the present invention, not intended to limit the present invention. Any modification, equivalent replacement, improvement and the like made within the spirit and principle of the present invention shall be included in the protection scope of the present invention.

We claim:

1. An analysis method for determining halogens in geological samples by ICP-MS, comprising the following steps:
   S1, weighing a geological sample and ammonium bifluoride and mixing, and heating at 200-220'C for 1-2 hours;
   S2, cooling to room temperature so as to obtain a solid mixture after heating is ended, adding ammonium hydroxide into the solid mixture, centrifuging, removing a precipitate, and collecting the supernatant;
   S3, adding an internal standard solution into the supernatant in the step S3, and uniformly mixing; and
   S4, optimizing the ICP-MS to an optimal state, testing content of chlorine in the supernatant under a condition of medium resolution, and testing content of bromine and iodine in the supernatant under a condition of low resolution.

2. The analysis method for determining halogens in geological samples by ICP-MS according to claim 1, wherein in the step S1, a mass ratio of the geological sample to the ammonium bifluoride is 1:(3-8).

3. The analysis method for determining halogens in geological samples by ICP-MS according to claim 1, wherein the geological sample comprises rock, soil or sediments; and the rock comprises granite, shale, basalt or andesite.

4. The analysis method for determining halogens in geological samples by ICP-MS according to claim 1, wherein in the step S2, the ammonium hydroxide has a concentration of 5% v/v.

5. The analysis method for determining halogens in geological samples by ICP-MS according to claim 1, wherein in the step S2, a centrifugal speed is 2500 r/min, and centrifugation time is 25 minutes.

6. The analysis method for determining halogens in geological samples by ICP-MS according to claim 1, wherein in the step S3, the internal standard solution is a 10 ng/g Te solution, and a medium of the 10 ng/g Te solution is the ammonium hydroxide having the concentration of 5% v/v.

7. The analysis method for determining halogens in geological samples by ICP-MS according to claim 1, wherein in the step S4, the optimal state of the optimized ICP-MS is that a signal of element In having a concentration of 1 ng/g is up to $10^6$ cps, and oxide yield $CeO^+/Ce^+$ is less than 2%.

8. The analysis method for determining halogens in geological samples by ICP-MS according to claim 1, wherein in the step S4, the condition of the medium resolution is m/Δm=4000 (in represents mass number and Δm represents mass difference), and the condition of the low resolution is m/Δm=300.

* * * * *